(12) United States Patent
de Josselin de Jong

(10) Patent No.: US 10,849,506 B2
(45) Date of Patent: Dec. 1, 2020

(54) BI-FREQUENCY DENTAL EXAMINATION

(71) Applicant: INSPEKTOR RESEARCH SYSTEMS B.V., Bussum (NL)

(72) Inventor: Elbert de Josselin de Jong, Bussum (NL)

(73) Assignee: INSPEKTOR RESEARCH SYSTEMS B.V., Bussum (NL)

( * ) Notice: Subject to any disclaimer, the term of this patent is extended or adjusted under 35 U.S.C. 154(b) by 122 days.

(21) Appl. No.: 16/093,866

(22) PCT Filed: Apr. 13, 2017

(86) PCT No.: PCT/IB2017/000513
§ 371 (c)(1),
(2) Date: Oct. 15, 2018

(87) PCT Pub. No.: WO2017/178889
PCT Pub. Date: Oct. 19, 2017

(65) Prior Publication Data
US 2019/0104943 A1 Apr. 11, 2019

Related U.S. Application Data

(60) Provisional application No. 62/321,968, filed on Apr. 13, 2016.

(51) Int. Cl.
*G06K 9/00* (2006.01)
*A61B 5/00* (2006.01)
(Continued)

(52) U.S. Cl.
CPC .......... *A61B 5/0088* (2013.01); *A61B 1/0005* (2013.01); *A61B 1/0638* (2013.01);
(Continued)

(58) Field of Classification Search
CPC . G06T 2207/10016; G06T 2207/10024; G06T 2207/10064; G06T 2207/10152;
(Continued)

(56) References Cited

U.S. PATENT DOCUMENTS 3,388,645 A  6/1968 Sullivan
3,424,070 A  1/1969 Nyman
(Continued)

FOREIGN PATENT DOCUMENTS

CN  1530073 A  9/2004
CN  1671320 A  9/2005
(Continued)

OTHER PUBLICATIONS

Singapore Office Action dated Oct. 23, 2019 for Application No. 11201809183X, 5 pages.
(Continued)

*Primary Examiner* — Amara Abdi
(74) *Attorney, Agent, or Firm* — Frost Brown Todd LLC

(57) ABSTRACT

A system and a method for improving visibility of newly decaying or carious tissue are described. Light having a lower peak wavelength (such as 405 nm) illuminates dental tissue, and an image is captured. Light having a higher peak wavelength (such as 450 nm) then illuminates the same dental tissue, and a second image is captured. The images are aligned, and an output image is created based on at least one of the first image and the second image, modified in certain areas as a function of the relationships between the red values of the first image ($R_1$) and the second image ($R_2$) at that location and the green values of the first image ($G_1$) and the second image ($G_2$) at that location. The function may use the ratios $R_2:R_1$ and $G_1:G_2$, such as a function of the product of those ratios, to determine the color adjustment that is applied.

20 Claims, 2 Drawing Sheets

(51) Int. Cl.
  *A61B 1/06* (2006.01)
  *A61B 1/24* (2006.01)
  *G06T 7/00* (2017.01)
  *G06T 7/90* (2017.01)
  *A61B 1/00* (2006.01)
  *G06T 5/00* (2006.01)

(52) U.S. Cl.
  CPC .............. *A61B 1/24* (2013.01); *A61B 5/0071* (2013.01); *A61B 5/4547* (2013.01); *G06T 5/008* (2013.01); *G06T 7/0012* (2013.01); *G06T 7/0014* (2013.01); *G06T 7/90* (2017.01); *G06T 2207/10016* (2013.01); *G06T 2207/10024* (2013.01); *G06T 2207/10064* (2013.01); *G06T 2207/10152* (2013.01); *G06T 2207/20221* (2013.01); *G06T 2207/30036* (2013.01)

(58) Field of Classification Search
  CPC . G06T 2207/20221; G06T 2207/30036; G06T 7/0012; G06T 7/90; G06T 7/0014; G06T 5/008; A61B 5/0088; A61B 5/4547; A61B 5/0071; A61B 1/0005; A61B 1/0638; A61B 1/24
  See application file for complete search history.

(56) References Cited

U.S. PATENT DOCUMENTS

| | | | |
|---|---|---|---|
| 3,711,700 A | 1/1973 | Westlund, Jr. et al. |
| 3,969,577 A | 7/1976 | Lloyd et al. |
| 3,971,954 A | 7/1976 | Kleinberg et al. |
| 4,080,476 A | 3/1978 | Laskey |
| 4,085,436 A | 4/1978 | Weiss |
| 4,266,535 A | 5/1981 | Moret |
| 4,290,433 A | 9/1981 | Alfano |
| 4,425,599 A | 1/1984 | Rieder et al. |
| 4,437,161 A | 3/1984 | Anderson |
| 4,445,858 A | 5/1984 | Johnson |
| 4,479,499 A | 10/1984 | Alfano |
| 4,515,476 A | 5/1985 | Ingmar |
| 4,591,784 A | 5/1986 | Kolitsch et al. |
| 4,615,679 A | 10/1986 | Wyatt |
| 4,662,843 A | 5/1987 | Croll |
| 4,706,296 A | 11/1987 | Pedotti et al. |
| 4,737,104 A | 4/1988 | Croll |
| 4,740,047 A | 4/1988 | Abe et al. |
| 4,836,206 A | 6/1989 | Maxwell et al. |
| 4,900,253 A | 2/1990 | Landis |
| 4,921,344 A | 5/1990 | Duplantis |
| 5,288,231 A | 2/1994 | Kuehn et al. |
| 5,306,144 A | 4/1994 | Hibst et al. |
| 5,359,513 A | 10/1994 | Kano et al. |
| 5,382,163 A | 1/1995 | Putnam |
| 5,408,992 A | 4/1995 | Hamlin et al. |
| 5,490,225 A | 2/1996 | Kumagai |
| 5,509,800 A | 4/1996 | Cunningham et al. |
| 5,528,432 A | 6/1996 | Donahoo |
| 5,590,660 A | 1/1997 | MacAulay et al. |
| 5,634,790 A | 6/1997 | Pathmanabhan et al. |
| 5,723,175 A | 3/1998 | Scholz et al. |
| 5,742,700 A | 4/1998 | Yoon et al. |
| 5,743,731 A | 4/1998 | Lares et al. |
| 5,779,634 A | 7/1998 | Ema et al. |
| 5,836,762 A | 11/1998 | Peithman |
| 5,865,621 A | 2/1999 | Calderwood |
| 5,894,620 A | 4/1999 | Polaert et al. |
| 5,957,687 A | 9/1999 | Brilliant |
| 6,015,290 A | 1/2000 | Rosenstatter |
| 6,022,214 A | 2/2000 | Hirsch et al. |
| 6,024,562 A | 2/2000 | Hibst et al. |
| 6,053,731 A | 4/2000 | Heckenberger |
| 6,132,210 A | 10/2000 | Lehmann |
| 6,132,211 A | 10/2000 | Peithman |
| 6,135,774 A | 10/2000 | Hack et al. |
| 6,149,430 A | 11/2000 | Nemetz et al. |
| 6,155,823 A | 12/2000 | Nagel |
| 6,186,780 B1 | 2/2001 | Hibst et al. |
| 6,201,880 B1 | 3/2001 | Elbaum et al. |
| 6,205,259 B1 | 3/2001 | Komiya et al. |
| 6,210,159 B1 | 4/2001 | Lehmann et al. |
| 6,227,850 B1 | 5/2001 | Chishti et al. |
| 6,231,338 B1 | 5/2001 | de Josselin de Jong et al. |
| 6,325,623 B1 | 12/2001 | Melnyk et al. |
| 6,332,033 B1 | 12/2001 | Qian |
| 6,345,982 B1 | 2/2002 | Meyer |
| 6,388,240 B2 | 5/2002 | Schulz et al. |
| 6,402,693 B1 | 6/2002 | Emery |
| 6,443,729 B1 | 9/2002 | Watson |
| 6,485,300 B1 | 11/2002 | Muller et al. |
| 6,512,994 B1 | 1/2003 | Sachdeva |
| 6,532,299 B1 | 3/2003 | Sachdeva et al. |
| 6,547,394 B2 | 4/2003 | Doherty |
| 6,561,802 B2 | 5/2003 | Alexander |
| 6,597,934 B1 | 7/2003 | de Josselin de Jong et al. |
| 6,769,911 B2 | 8/2004 | Buchalla et al. |
| 6,788,813 B2 | 9/2004 | Cooper |
| 6,860,879 B2 | 3/2005 | Irion et al. |
| 6,960,165 B2 | 11/2005 | Ueno et al. |
| 6,964,567 B2 | 11/2005 | Kerschbaumer et al. |
| 7,234,937 B2 | 6/2007 | Sachdeva et al. |
| 7,365,844 B2 | 4/2008 | Richards-Kortum et al. |
| 7,570,984 B2 | 8/2009 | Katsuda et al. |
| 7,813,787 B2 | 10/2010 | de Josselin de Jong et al. |
| 7,813,790 B2 | 10/2010 | de Josselin de Jong et al. |
| 8,270,689 B2 | 9/2012 | Liang et al. |
| 8,363,912 B2 | 1/2013 | Thoms |
| 9,918,641 B2 | 3/2018 | de Josselin de Jong |
| 2001/0010760 A1 | 8/2001 | Saito |
| 2003/0156788 A1 | 8/2003 | Henning |
| 2004/0225340 A1 | 11/2004 | Evans |
| 2004/0240716 A1 | 12/2004 | de Josselin de Jong et al. |
| 2004/0254478 A1 | 12/2004 | de Josselin de Jong et al. |
| 2005/0080465 A1 | 4/2005 | Zelickson et al. |
| 2008/0062429 A1 | 3/2008 | Liang et al. |
| 2008/0082000 A1* | 4/2008 | Thoms .................. A61B 1/043 600/476 |
| 2008/0170764 A1 | 7/2008 | Burns et al. |
| 2012/0201451 A1* | 8/2012 | Bryant ................ H04N 1/6075 382/164 |
| 2018/0289240 A1* | 10/2018 | Aoyama ............ A61B 1/00006 |

FOREIGN PATENT DOCUMENTS

| | | |
|---|---|---|
| CN | 101528116 A | 9/2009 |
| DE | 33 45 465 A | 6/1985 |
| DE | 40 32 779 A1 | 4/1992 |
| DE | 20 209 441 U1 | 9/2002 |
| EP | 0 068 286 A2 | 1/1983 |
| EP | 1 252 858 A2 | 10/2002 |
| EP | 2 078 493 A2 | 7/2009 |
| EP | 2401958 A1 | 1/2012 |
| GB | 2 256 938 A | 12/1992 |
| GB | 2 340 618 A | 2/2002 |
| JP | H05-337142 A | 12/1993 |
| JP | H09-189659 A | 7/1997 |
| JP | H10-309290 A | 11/1998 |
| JP | H11-42242 A | 2/1999 |
| JP | 2001-299699 A | 10/2001 |
| JP | 2002-355263 A | 12/2002 |
| JP | 2003-007478 A | 1/2003 |
| JP | 2004-089236 A | 3/2004 |
| JP | 2004-521714 A | 7/2004 |
| JP | 2004-237081 A | 8/2004 |
| JP | 2004-526550 A | 9/2004 |
| JP | 2004-313783 A | 11/2004 |
| JP | 2007-151782 A | 6/2007 |
| JP | 2009-165831 A | 7/2009 |
| JP | 2015-029692 A | 2/2015 |
| KR | 2004-0005408 A | 1/2004 |
| KR | 2004-0065178 A | 7/2004 |
| RU | 2464549 C1 | 10/2012 |

(56) References Cited

FOREIGN PATENT DOCUMENTS

| | | |
|---|---|---|
| RU | 2538614 C1 | 1/2015 |
| RU | 2556568 C2 | 7/2015 |
| RU | 2570966 C2 | 12/2015 |
| WO | WO 90/12541 A1 | 11/1990 |
| WO | WO 99/28698 A2 | 6/1999 |
| WO | WO 99/58043 A2 | 11/1999 |
| WO | WO 99/59462 A1 | 11/1999 |
| WO | WO 00/21450 A1 | 4/2000 |
| WO | WO 02/43604 A2 | 6/2002 |
| WO | WO 02/061683 A2 | 8/2002 |
| WO | WO 2004/012593 A1 | 2/2004 |
| WO | WO 2004/093673 A1 | 11/2004 |
| WO | WO 2008/033218 A1 | 3/2008 |
| WO | WO 2010/025122 A1 | 3/2010 |
| WO | WO 2016/073569 A2 | 5/2016 |

OTHER PUBLICATIONS

Albin, S., et al., "Laser Induced Fluorescence of Dental Caries," SPIE, 1988, 907:96-98, XP000570174, 5 pgs.
Angmar-Månsson, B., et al., "Quantitative light-induced fluorescence (QLF): a method for assessment of incipient caries lesions," Dentomaxillofacial Radiology, Nov. 2001, 30(6):298-307, 10 pgs.
Cheng, H.D., et al., "Color image segmentation: advances and prospects," Pattern Recognition, Dec. 2001, 34(12):2259-2281, 43 pgs.
Fisher, M., et al., "Tooth-Caries Early Diagnosis and Mapping by Fourier Transform Spectral Imaging Fluorescence," Instrumentation Science & Technology, 2002, 30(2):225-232, 8 pgs.
Heinrich-Weltzien, R., et al., "Quantitative light-induced fluorescence (QLF)—A potential method for the dental practitioner," Quintessence International, 2003, 34(3):181-188, 8 pgs.
Jain, A.K., "Scene Matching and Detection" Chap. 9, Sec. 9.12, *Fundamentals of Image Processing*, 1989, Prentice Hall, USA, pp. 400-407, 14 pgs.
Karl Storz Autofluorescence System—P020008, Summary of Safety and Effectiveness, U.S. Food and Drug Administration, Center for Devices and Radiological Health, Feb. 6, 2003, 21 pgs.
Lehmann, T.M., et al., "A Comparison of Similarity Measures for Digital Subtraction Radiography," Comput Biol Med, 1997, 27(2):151-167, 17 pgs.
Lehmann, T.M., et al., "Computer-based registration for digital subtraction in dental radiology," Dentomaxillofacial Radiology, 2000, 29:323-346, 24 pgs.
Lehmann, T.M., et al., "Image processing and enhancement provided by commercial dental software programs," Dentomaxillofacial Radiology, Jul. 2002, 31(4):264-272, 9 pgs.
Lucey, S., et al., "A Suitability Metric for Mouth Tracking Through Chromatic Segmentation," IEEE Proceedings 2001 International Conference on Imagine Processing (ICIP), Oct. 7-10, 2001, vol. III, pp. 258-261, 4 pgs.
Pretty, I.A., et al., "The effect of ambient light on QLF analyses," J Oral Rehabil, Apr. 2002, 29(4):369-373, 5 pgs.
Uenohara, M., et al., "Vision-Based Object Registration for Real-Time Image Overlay," In: Ayache, N. (eds) Computer Vision, Virtual Reality and Robotics in Medicine. CVRMed 1995, Lecture Notes in Computer Science, vol. 905, Springer, Berlin, Heidelberg, 10 pgs.
Van Der Stelt, P.F., "Impact of Digital Radiology—The advantages of the Emago® software package," Oral Diagnostic Systems, Amsterdam, 1998, 4 pgs.
Australian Office Action, Examination Report No. 1 for standard patent application, dated Jun. 8, 2017 for Application No. AU 2013326222, 5 pgs.
Canadian Office Action dated Feb. 26, 2009 for Application No. CA 2,520,195, 3 pgs.
Canadian Office Action dated Apr. 26, 2010 for Application No. CA 2,520,195, 2 pgs.
Canadian Office Action dated Oct. 2, 2018 for Application No. CA 2,886,768, 3 pgs.
Chinese Office Action, The First Office Action, and First Search Report dated Jun. 30, 2016 for Application No. CN 201380051343. 4, 13 pgs.
Chinese Office Action, Notification of Second Office Action, dated May 15, 2017 for Application No. CN 201380051343.4, 7 pgs.
European Communication dated Mar. 23, 2007 for Application No. EP 01273549.4, 3 pgs.
European Communication dated May 30, 2006 for Application No. EP 03766529.6, 3 pgs.
European Comunication, Decision to Grant, dated Sep. 6, 2007 for Application No. EP 03766529.6, 2 pgs.
European Communication dated Aug. 30, 2006 for Application No. EP 04734476.7, 4 pgs.
European Communication dated Apr. 7, 2008 for Application No. EP 04734476.7, 4 pgs.
European Communication dated Sep. 28, 2011 for Application No. EP 04734476.7, 5 pgs.
European Communication dated Sep. 13, 2017 for Application No. EP 13830087.6, 4 pgs.
European Communication dated Jul. 10, 2018 for Application No. EP 13830087.6, 5 pgs.
European Communication dated Mar. 1, 2019 for Application No. EP 13830087.6, 4 pgs.
International Search Report dated Sep. 25, 2002 for Application No. PCT/IB2001/02862, 3 pgs.
International Written Opinion dated Oct. 10, 2002 for Application No. PCT/IB2001/02862, 6 pgs.
International Preliminary Examination Report dated Mar. 4, 2003 for Application No. PCT/IB2001/02862, 14 pgs.
International Search Report dated Dec. 4, 2003 for Application No. PCT/IB2003/03024, 4 pgs.
International Written Opinion dated May 27, 2004 for Application No. PCT/IB2003/03024, 4 pgs.
International Preliminary Examination Report dated Oct. 27, 2004 for Application No. PCT/IB2003/03024, 9 pgs.
International Search Report and Written Opinion dated Nov. 30, 2004 for Application No. PCT/IB2004/001655, 12 pgs.
International Preliminary Report on Patentability dated Jun. 23, 2005 for Application No. PCT/IB2004/001655, 6 pgs.
International Search Report and Written Opinion dated Apr. 27, 2005 for Application No. PCT/IB2004/001658, 17 pgs.
International Preliminary Report on Patentability dated Aug. 26, 2005 for Application No. PCT/IB2004/001658, 19 pgs.
International Search Report and Written Opinion dated Apr. 23, 2014 for Application No. PCT/IB2013/002791, 11 pgs.
International Preliminary Report on Patentability dated Jan. 27, 2015 for Application No. PCT/IB2013/002791, 17 pgs.
International Search Report and Written Opinion dated Aug. 17, 2017 for Application No. PCT/IB2017/00513, 11 pgs.
Israeli Office Action dated Jun. 12, 2018 for Application No. IL 238000, 3 pgs.
Japanese Office Action, Notification of Reasons for Refusal, dated Apr. 2, 2010 for Application No. JP 2004-370295, 3 pgs.
Japanese Office Action, Decision to Grant a Patent, dated Dec. 1, 2010 for Application No. JP 2004-370295, 3 pgs.
Japanese Office Action, Notification of Reasons for Refusal, dated Jan. 15, 2010 for Application No. JP 2006-530673, 3 pgs.
Japanese Office Action, Final Notification of Reasons for Refusal, dated Aug. 11, 2010 for Application No. JP 2006-530673, 2 pgs.
Japanese Office Action, Final Notification of Reasons for Refusal, dated Jul. 26, 2011 for Application No. JP 2006-530673, 2 pgs.
Japanese Office Action, Decision of Refusal, dated Apr. 3, 2012 for Application No. JP 2006-530673, 1 pg.
Japanese Office Action, Notification of Reasons for Refusal, dated Jan. 13, 2010 for Application No. JP 2006-530674, 3 pgs.
Japanese Office Action, Notification of Reasons for Refusal, dated Aug. 6, 2010 for Application No. JP 2006-530674, 3 pgs.
Japanese Office Action, Decision of Refusal, dated Apr. 7, 2011 for Application No. JP 2006-530674, 1 pg.
Japanese Office Action, Notice of Reasons for Rejection, dated Jul. 19, 2017 for Application No. JP 2015-533715, 23 pgs.

(56) References Cited

OTHER PUBLICATIONS

Japanese Search Report by Registered Searching Organization dated Jul. 19, 2017 for Application No. JP 2015-533715, 7 pgs.
Japanese Office Action, Decision of Refusal, dated Jan. 23, 2018 for Application No. JP 2015-533715, 6 pgs.
Japanese Office Action, Report of Reconsideration by Examiner before Appeal, dated Jun. 14, 2018 for Application No. JP 2015-533715, Appeal No. 2018-007015, 5 pgs.
Japanese Written Statement submitted by applicant in response to Report of Reconsideration by Examiner before Appeal, dated Sep. 19, 2018 for Application No. JP 2015-533715, Appeal No. 2018-007015, 6 pgs.
Japanese Office Action, Notification of Reasons for Refusal, dated Jun. 14, 2018 for Application No. JP 2017-202638, 2 pgs.
Japanese Office Action, Decision of Refusal, dated Dec. 25, 2018 for Application No. JP 2017-202638, 2 pgs.
Korean Office Action, Notification of Reason for Refusal, dated May 16, 2018 for Application No. KR 2015-7011526, 4 pgs.
Korean Office Action, Notification of Reason for Refusal, dated Oct. 11, 2018 for Application No. KR 2015-7011526, 4 pgs.
Korean Office Action, Notice of Final Rejection, dated Feb. 28, 2019 for Application No. KR 2015-7011526, 3 pgs.
Mexican Office Action dated Jun. 22, 2016 for Application No. MX/a/2015/004158, 3 pgs.
Vietnamese Office Action dated May 4, 2018 for Application No. VN 1-2015-01031, 2 pgs.
Russian Office Action and Search Report dated Oct. 5, 2020 for Application No. 2018139705, 6 pages.

\* cited by examiner

BI-FREQUENCY DENTAL EXAMINATION

FIELD

The present invention relates to examining oral structures to identify carious regions. More specifically, the present invention relates to systems and methods for inducing autofluorescence of oral structures and analyzing images thereof to differentiate between dental surfaces covered with dental plaque and clean surfaces, and the detection of carious lesions.

BACKGROUND

With the traditional QLF technique (excitation with light having a peak wavelength of about 405 nm and image capture with a long-pass yellow filter or filter blocking the excitation light) the fluorescence of porphyrins produced by active bacteria in the intra-oral environment can be imaged as these appear with a red color compared to sound teeth by a camera or by the eye.

The traditional method thus visualizes plaque covering a tooth relative to its clean surface.

Early (young) plaque (less than 3 days old) is difficult to distinguish in this way, as the contrast is low between plaque covered and uncovered areas. Only plaque older than 3-5 days can be readily detected.

SUMMARY

A solution is presented to detect the red fluorescence of young plaque with higher sensitivity and specificity than with the traditional method.

One embodiment according to the present disclosure is a device, system, or kit that includes lighting elements, which provide incident light with a peak wavelength at about 405 nm and about 450 nm, respectively. The respective lighting elements are separately energized, and the fluorescence of dental tissues under the respective lights are captured through a long-pass filter (having a preferred cutoff frequency at 520 nm) in separate images. The images are manipulated so that the portions of the respective images that relate to the same physical location on the dental tissues can be accessed. A new image is created as a function of the values of the red and green channels from the respective images, including the baseline image plus an overlay wherein each pixel or region is selected as a function of those red and green channels. In variations on this embodiment, the longer-wavelength lighting elements have a peak in the 430-490 nm range, and the filter has a corresponding cutoff frequency in the 440-540 nm range.

In other variations, the output is a function of a ratio of ratios, where the numerator is the ratio of red channel intensity under the longer-wavelength incident light to the red channel intensity under the shorter-wavelength incident light, and the denominator is the ratio of green channel intensity under the longer-wavelength incident light to the green channel intensity under the shorter-wavelength incident light. This ratio can be shifted and scaled to meet a variety of potential intended output contexts as will occur to those skilled in the art in view of this disclosure.

Another embodiment is a method of displaying or examining dental issue. A light having a peak wavelength of about 405 nm is shined on the dental tissue, and the fluorescence generated is passed through a long-pass filter (having a cutoff frequency of about 520 nm) and captured as first digital image. The 405 nm light is extinguished, and a light having a peak wavelength of about 450 nm is illuminated. The fluorescence generated is likewise passed through the long-pass filter and captured as a second digital image. The images are aligned, and output (as described above) is generated as a function of both images.

DESCRIPTION

Figure 1:
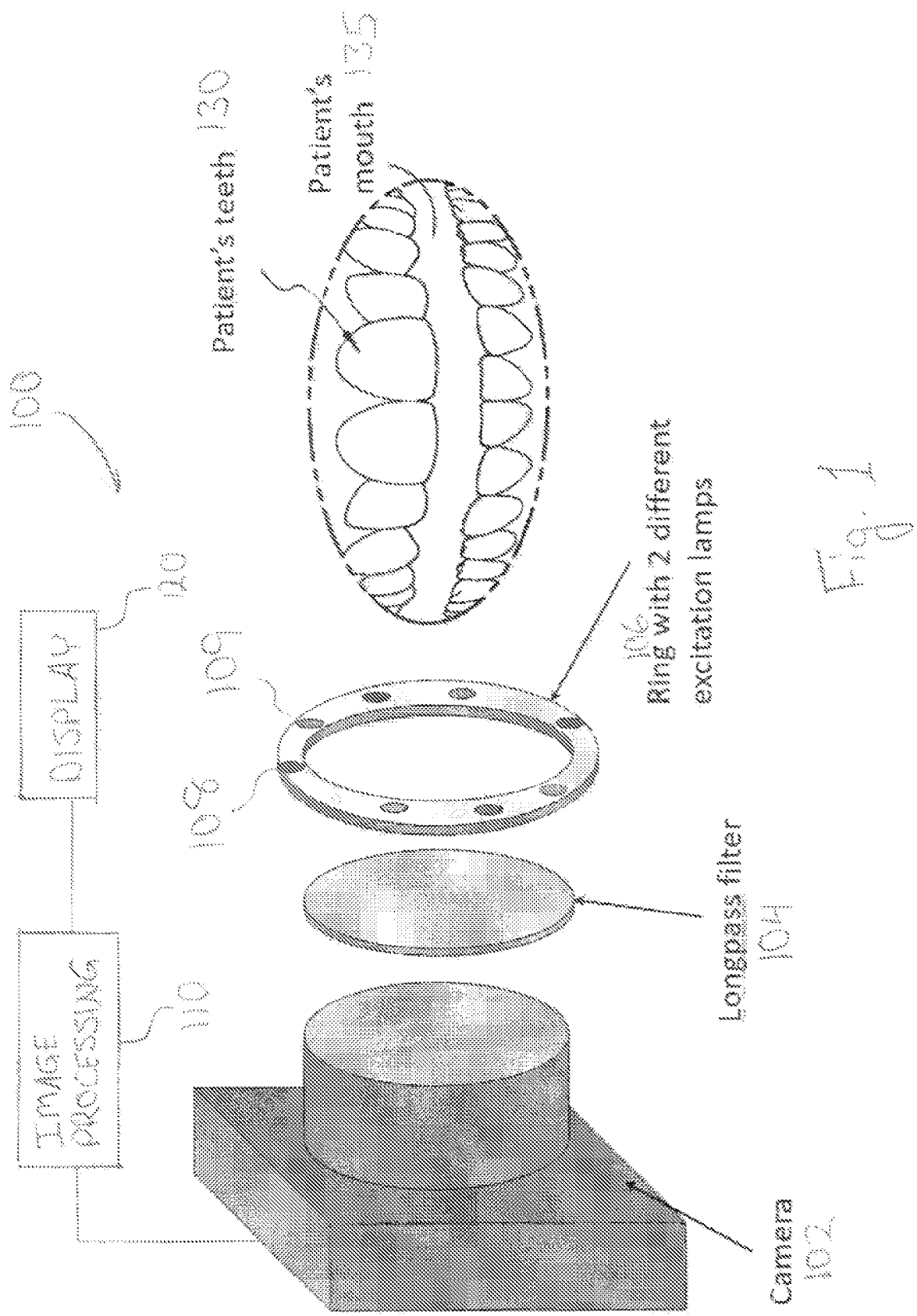
FIG. 1 is a schematic view of a system for capturing and analyzing images according to one embodiment of the present disclosure.

For the purpose of promoting an understanding of the principles of the present invention, reference will now be made to the embodiment illustrated in the drawings and specific language will be used to describe the same. It will, nevertheless, be understood that no limitation of the scope of the invention is thereby intended; any alterations and further modifications of the described or illustrated embodiments, and any further applications of the principles of the invention as illustrated therein are contemplated as would normally occur to one skilled in the art to which the invention relates.

Generally, one form of the present system shines light of about 405 nm on dental tissue and captures a filtered image of that tissue, then shines light of about 450 nm on the dental tissue and captures a filtered image of that tissue. The images are automatically aligned, and the respective images at each pixel of tissue surface are analyzed. In some embodiments of this form, and output image is generated with additional data (such as a certain color) overlaid to indicate carious tissue. In other embodiments, a spectrum of colors and/or a sliding scale of hue, intensity, alpha level, or other characteristics are used to illustrate a detected age of the lesion.

Figure 2:
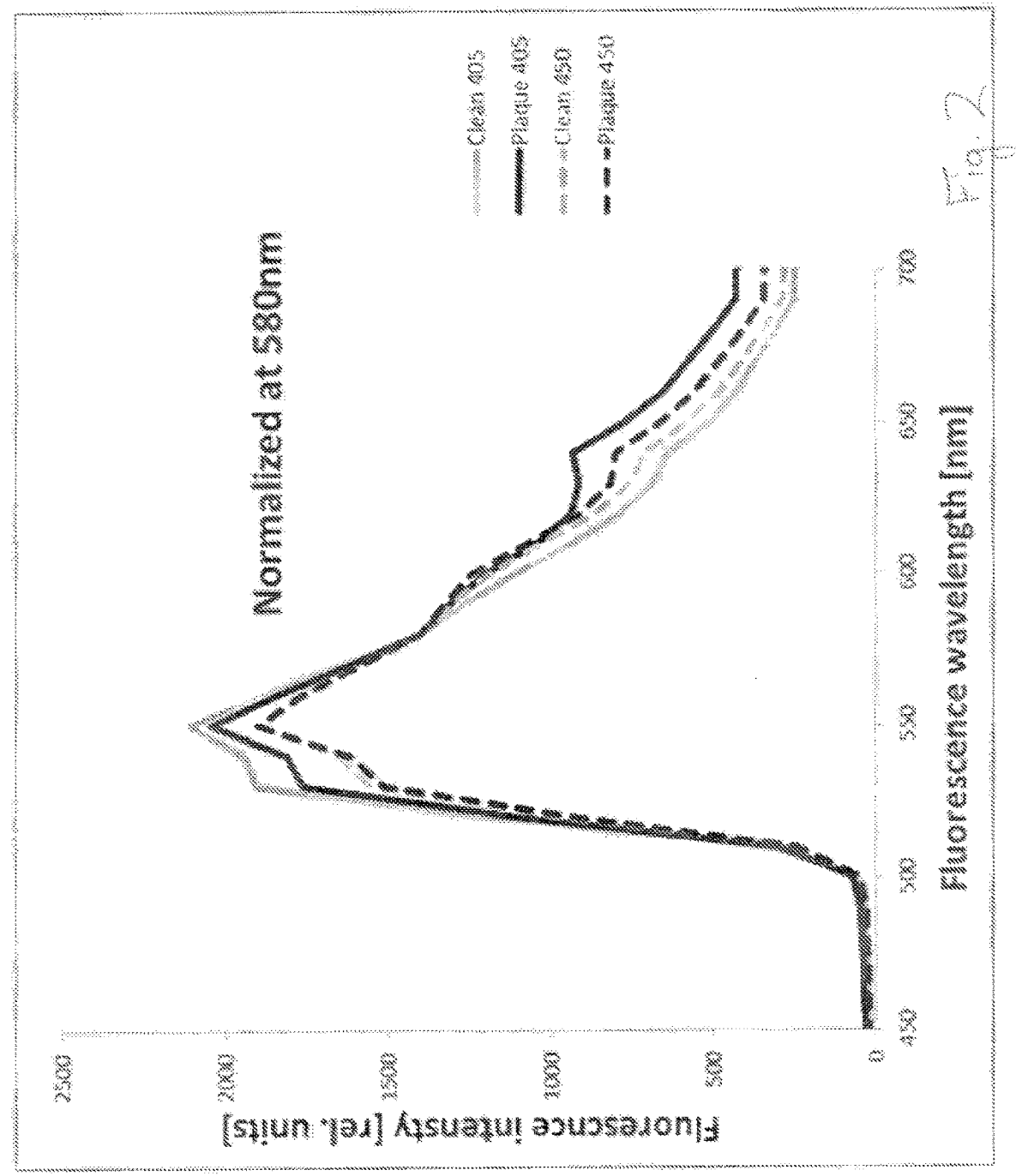
FIG. 2 is an exemplary graph of autofluorescence responses from healthy and carious tooth tissue under 405 nm and 450 nm incident light.

The discussion herein takes advantage of the data illustrated in FIG. 2, namely, that clean and carious tooth tissues have different autofluorescence responses when exposed to incident light around the 405 nm and 450 nm wavelengths. These graphs provide visualization of data captured by a multispectral camera, where each curve has been normalized at 580 nm. As can be seen in FIG. 2, while clean tissue fluoresces more than young plaque at lower wavelengths (in the green portion of the visible spectrum) and less than young plaque at higher (red) wavelengths under incident light of 405 nm, while under incident light of 450 nm, clean tissue and young plaque fluoresce about the same in the green range while diverging (with young plaque fluorescing more) in the red range.

Turning to FIG. 1, system 100 includes a camera 102 configured to capture images through long-pass filter 104. In this embodiment, ring 106 is generally annular and bears a plurality of lighting elements that includes 405 nm LEDs 108 and 450 nm LEDs 109. Ring 106 is situated around the circumference of the front of camera 102 or long-pass filter 104 so that LEDs 108, 109 emit their light substantially along the optical axis of camera 102. The output of camera 102 is in communication with image processing apparatus 110, which in this embodiment produces human-viewable output via display 120.

In operation, system 100 might be used to evaluate, diagnose, or characterize the condition of one or more of a patient's teeth 130. To this end, camera 102 is pointed in the general direction of patient's mouth 135 and focused on patient's teeth 130. In some embodiments, this focusing operation occurs manually, while in others it occurs automatically using digital or optical techniques as will occur to those skilled in the art. In some embodiments, focusing occurs using one or more lighting elements on ring 106, and in some embodiments focusing occurs using ambient and/or white light from another source (not shown).

System 100 then captures two images as will now be discussed. The first set of LEDs 108 on ring 106 is energized, exposing the patient's teeth 130 to incident light having a peak wavelength of about 405 nm. Patient's teeth 130 then differentially autofluorescence as is well understood in the art, including as described in U.S. Pat. Nos. 6,231,338, 7,813,787, and 7,813,790. Long-pass filter 104 filters the light resulting from fluorescence of patient's teeth 130, and camera 102 captures the filtered light as a first image.

The first set of LEDs 108 on ring 106 is then deenergized, and the second set of LEDs 109 on ring 106 is energized, exposing patient's teeth 130 to incident light having a peak wavelength at about 450 nm. Patient's teeth 130 then differentially autofluorescence in a slightly different way (see FIG. 2), long-pass filter 104 filters the light resulting from the autofluorescence, and camera 102 captures a second image.

Image processing device 110 receives the two images from camera 102, puts them in the same position and thus comparable so that the pixels derived from each image that correspond with the same location on patient's teeth 130 can be mathematically operated upon. Various techniques known to those skilled in the art can be used for this repositioning, or "registration," step. In some embodiments, the second image is automatically selected from a video stream by an automatic system that compares the first image (taken under LEDs 108) with each frame of the video stream (taken under LEDs 109) until a sufficiently registered frame is found and captured. One exemplary dynamic comparison technique is shown in U.S. Pat. No. 6,597,934, but other techniques may be used as will occur to those skilled in the art.

Image processing device 110 then produces an output image wherein the visual components of each pixel are a function of the color values of pixels derived from corresponding positions on the two input images. In some forms of the present embodiment, the output pixel is calculated as $$G_{pix} = \left(1 - \left|\frac{R_{450nm}}{R_{450nm}} \cdot \frac{G_{405nm}}{G_{450nm}}\right| \beta\right) \cdot \alpha$$

where a is a scaling constant, β is a constant that biases the result to a desired range, single-color pixel values $R_{450\ nm}$, $R_{405\ nm}$, $G_{405\ nm}$, and $G_{450\ nm}$ are the red or green pixel color values in the image captured under incident light of the indicated frequency, and $G_{pix}$. In some embodiments, β is a function of the optical properties of the equipment being used; empirical data regarding relative pixel values $R_{450\ nm}$, $R_{405\ nm}$, $G_{405\ nm}$, and $G_{450\ nm}$; and/or the intended downstream uses of $G_{pix}$.

In one implementation of the embodiment illustrated in FIG. 1, image processing device 110 creates one of two kinds of images for display on display device 120. In one kind of image, the output image is constructed of red, blue, and green channels, where the blue and green channels are chosen as a function of the overall brightness of the original images at that pixel location (e.g., $(R_{405\ nm}+R_{450\ nm}+G_{405\ nm}+G_{450\ nm}+B_{405\ nm}+B_{450\ nm})/6$), and the red channel is $G_{pix}$.

Another kind of image is generated in some embodiments by creating a base image that takes the average of the respective pixel color values from each channel of the original images, then overlays color as a function of $G_{pix}$ at that location. In some embodiments, this overlay is a constant, bright red whenever $G_{pix}$ exceeds a particular threshold at that location. In other embodiments, the overlay is a red color that is adjusted in brightness as a function of $G_{pix}$ (e.g., where both the red channel R of the output image and $G_{pix}$ are on a 0-255 scale, $R=128+(G_{pix}/2)$). In yet other embodiments, the base image is a third image captured under white light or a color-corrected version of one or both of the images captured under LEDs 108 and/or 109. In still other embodiments, the color of the output pixel is selected to have a hue, alpha value, brightness, or other characteristic that varies with $G_{pix}$.

Thus, one method of examining dental tissues includes illuminating dental tissues with a 405 nm light, filtering the fluorescence produced through a long-pass filter having a cutoff frequency of about 520 nm, and capturing a first image. A 450 nm light is then illuminated, the fluorescence produced is likewise passed through the long-pass filter, and a second image is captured. The two images are analyzed to determine how to map respective portions of each image to the dental tissue and/or particular positions, and output is generated as a function of one or two color components of the first and second images at the respective points related to the same portion of tissue.

The various image processing activities performed by the various implementations of this system and method are implemented using special programming stored in a memory device and executed by a processor, all as will occur to those skilled in the art. For example, an "image processing device," as this example has generically been referred to, includes a processor in communication with a memory, input interface(s), output interface(s), and a network interface. The memory stores a variety of data, but is also encoded with programming instructions executable to perform the functions described. Power, ground, clock, and other signals and circuitry are used as appropriate as will be understood and easily implemented by those skilled in the art.

The network interface connects the computer to a data network for communication of data between the computer and other devices attached to a data network, such as cellular, satellite, Wi-Fi, WiMAX, or other system as will occur to those skilled in the art. The input interface(s) manage communication between the processor and one or more touch screens, sensors, pushbuttons, UARTs, IR and/or RF receivers or transceivers, decoders, or other devices, as well as traditional keyboard and mouse devices. Output interface(s) provide a video signal to a display, and may provide signals to one or more additional output devices such as LEDs, LCDs, or audio output devices, local multimedia devices, local notification devices, or a combination of these and other output devices and techniques as will occur to those skilled in the art.

The processor in some embodiments is a microcontroller, graphics processing unit, accelerated processing unit, or general-purpose microprocessor that reads its program from the memory. The processor may be comprised of one or more components configured as a single unit. Alternatively, when of a multi-component form, the processor may have one or more components located remotely relative to the others. One or more components of the processor may be of the electronic variety including digital circuitry, analog circuitry, or both. In some embodiments, the processor is of a conventional, integrated circuit microprocessor arrangement, such as one or more CORE i3, i5, or i7 processors from INTEL Corporation of 2200 Mission College Boulevard, Santa Clara, Calif. 95052, USA, or SEMPRON, ATHLON, or A-Series processors from Advanced Micro Devices, One AMD Place, Sunnyvale, Calif. 94088, USA. In some embodiments, one or more reduced instruction set computer (RISC) processors, graphics processing units (GPU), application-specific integrated circuits (ASICs), general-purpose microprocessors, programmable logic arrays, engine control units, or other devices may be used alone or in combinations as will occur to those skilled in the art.

Likewise, the memory in various embodiments includes one or more types such as solid-state electronic memory, magnetic memory, or optical memory, just to name a few. By way of non-limiting example, the memory can include solid-state electronic Random Access Memory (RAM), Sequentially Accessible Memory (SAM) (such as the First-In, First-Out (FIFO) variety or the Last-In First-Out (LIFO) variety), Programmable Read-Only Memory (PROM), Electrically Programmable Read-Only Memory (EPROM), or Electrically Erasable Programmable Read-Only Memory (EEPROM); an optical disc memory (such as a recordable, rewritable, or read-only DVD or CD-ROM); a magnetically encoded hard drive, floppy disk, tape, or cartridge medium; a solid-state or hybrid drive; or a plurality and/or combination of these memory types. Also, the memory in various embodiments is volatile, nonvolatile, or a hybrid combination of volatile and nonvolatile varieties of non-transitory signal.

When an act is described herein as occurring "as a function of" a particular thing, the system is configured so that the act is performed in different ways depending on the identity or one or more other characteristics of the thing.

All publications, prior applications, and other documents cited herein are hereby incorporated by reference in their entirety as if each had been individually incorporated by reference and fully set forth. While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A system for visually examining dental tissue, comprising:
   a first light having a first peak wavelength;
   a second light having a second peak wavelength that is at least 10 nm longer than the first peak wavelength;
   a processor;
   a memory in communication with the processor, the memory storing programming instructions executable by the processor to:
      capture a first image of dental tissue under the first light;
      capture a second image of the dental tissue under the second light;
      determine a first red value and a first green value associated with a point on the dental tissue as shown in the first image;
      determine a second red value and a second green value associated with the point on the dental tissue as shown in the second image;
      create a third image of the dental tissue, where a portion of the third image depicting the point on the dental tissue is adapted using a modification function that is a function of both
         (i) a ratio of the first red value to the second red value, and
         (ii) a ratio of the first green value to the second green value.

2. The system of claim 1, wherein the modification function is further a function of:
   the ratio of the second red value to the first red value, times
   the ratio of the first green value to the second green value.

3. The system of claim 1, wherein the modification function is further a function of $G_{pix}$, where:

$$G_{pix} = \left(1 - \frac{R_{450nm}}{R_{405nm}} \cdot \frac{G_{405nm}}{G_{450nm}} + \beta\right) \cdot \alpha.$$

4. The system of claim 3, wherein in portions of the third image in which $G_p$ix exceeds a predetermined threshold, the adaptation increases the brightness of such portions relative to the remaining portions of the third image.

5. The system of claim 3, wherein in portions of the third image in which $G_p$ix exceeds a predetermined threshold, the adaptation increases the intensity in the red color channel of such portions relative to the remaining portions of the third image.

6. The system of claim 1, wherein the adaptation is a change to a hue, alpha value, or brightness of the portion of the third image.

7. The system of claim 1,
   further comprising a display; and
   wherein the programming instructions are further executable by the processor to show the third image on the display.

8. The system of claim 1,
   further comprising a nonvolatile storage device; and
   wherein the programming instructions are further executable by the processor to save the third image to the nonvolatile storage device.

9. The system of claim 1, wherein:
   the first peak wavelength is at least 400 nm and not more than 410 nm; and
   the second peak wavelength is at least 415 nm and not more than 500 nm.

10. The system of claim 1, wherein:
    the first peak wavelength is about 405 nm; and
    the second peak wavelength is about 450 nm.

11. A method of observing dental tissue, comprising:
    illuminating the dental tissue with a first light having a first peak wavelength and capturing a first image of the dental tissue;
    illuminating the dental tissue and a second light having a second peak wavelength and capturing a second image of the dental tissue;
    determining a first red value and a first green value associated with a point on the dental tissue as shown in the first image;
    determining a second red value and a second green value associated with the point on the dental tissue as shown in the second image;

creating a third image of the dental tissue, where a portion of the third image depicting the point on the dental tissue is adapted using a modification function that is a function of both
  (i) a ratio of the first red value to the second red value, and
  (ii) a ratio of the first green value to the second green value.

12. The method of claim 11, wherein the modification function is further a function of:
  the ratio of the second red value to the first red value, times
  the ratio of the first green value to the second green value.

13. The method of claim 11, wherein the modification function is further a function of $G_{pix}$, where:

$$G_{pix} = \left(1 - \frac{R_{450nm}}{R_{405nm}} \cdot \frac{G_{405nm}}{G_{450nm}} + \beta\right) \cdot \alpha.$$

14. The method of claim 13, wherein the adaptation is to increase the brightness of portions of the third image in which $G_{pix}$ exceeds a predetermined threshold.

15. The method of claim 13, wherein the adaptation is to increase the intensity in the red color channel of portions of the third image in which $G_{pix}$ exceeds a predetermined threshold.

16. The method of claim 11, wherein the adaptation is a change to a hue, alpha value, or brightness of the portion of the third image.

17. The method of claim 11,
further comprising a display; and
wherein the programming instructions are further executable by the processor to show the third image on the display.

18. The method of claim 11,
further comprising a nonvolatile storage device; and
wherein the programming instructions are further executable by the processor to save the third image to the nonvolatile storage device.

19. The method of claim 11, wherein:
the first peak wavelength is at least 400 nm and not more than 410 nm; and
the second peak wavelength is at least 415 nm and not more than 500 nm.

20. The method of claim 11, wherein:
the first peak wavelength is about 405 nm; and
the second peak wavelength is about 450 nm.

* * * * *